US008185553B2

(12) United States Patent
Carus et al.

(10) Patent No.: US 8,185,553 B2
(45) Date of Patent: May 22, 2012

(54) CATEGORIZATION OF INFORMATION USING NATURAL LANGUAGE PROCESSING AND PREDEFINED TEMPLATES

(75) Inventors: Alwin B. Carus, Waban, MA (US); Harry J. Ogrinc, Westwood, MA (US)

(73) Assignee: Dictaphone Corporation, Stratford, CT (US)

( * ) Notice: Subject to any disclaimer, the term of this patent is extended or adjusted under 35 U.S.C. 154(b) by 203 days.

(21) Appl. No.: 12/121,527

(22) Filed: May 15, 2008

(65) Prior Publication Data
US 2008/0255884 A1 Oct. 16, 2008

Related U.S. Application Data

(63) Continuation of application No. 10/840,428, filed on May 7, 2004, now Pat. No. 7,379,946.

(60) Provisional application No. 60/557,834, filed on Mar. 31, 2004.

(51) Int. Cl.
*G06F 17/30* (2006.01)
(52) U.S. Cl. ......... 707/791; 707/802; 707/822; 707/808
(58) Field of Classification Search ........... 707/600–831
See application file for complete search history.

(56) References Cited

U.S. PATENT DOCUMENTS

| | | |
|---|---|---|
| 4,477,698 A | 10/1984 | Szlam et al. |
| 4,965,763 A | 10/1990 | Zamora |
| 5,253,164 A | 10/1993 | Holloway et al. |
| 5,325,293 A | 6/1994 | Dorne |
| 5,327,341 A | 7/1994 | Whalen et al. |
| 5,392,209 A | 2/1995 | Eason et al. |
| 5,544,360 A | 8/1996 | Lewak et al. |
| 5,664,109 A | 9/1997 | Johnson et al. |
| 5,675,788 A | 10/1997 | Husick et al. |
| 5,799,268 A | 8/1998 | Boguraev |
| 5,809,479 A | 9/1998 | Martin et al. |
| 5,832,450 A | 11/1998 | Myers et al. |
| 5,893,109 A | 4/1999 | DeRose et al. |
| 5,970,463 A | 10/1999 | Cave et al. |
| 5,974,412 A | 10/1999 | Hazlehurst et al. |
| 6,006,221 A | 12/1999 | Liddy et al. |
| 6,014,663 A | 1/2000 | Rivette et al. |
| 6,021,202 A | 2/2000 | Anderson et al. |
| 6,052,693 A | 4/2000 | Smith et al. |
| 6,055,494 A | 4/2000 | Friedman |
| 6,088,437 A | 7/2000 | Amick |

(Continued)

OTHER PUBLICATIONS

U.S. Appl. No. 10/840,428, filed May 7, 2004, Carus et al.

(Continued)

*Primary Examiner* — Isaac M Woo
(74) *Attorney, Agent, or Firm* — Wolf, Greenfield & Sacks, P.C.

(57) ABSTRACT

A computer implemented method for generating a report that includes latent information, comprising receiving an input data stream that includes latent information, performing one of normalization, validation, and extraction of the input data stream, processing the input data stream to identify latent information within the data stream that is required for generation of a particular report, wherein said processing of the input data stream to identify latent information comprises of identifying a relevant portion of the input data stream, bounding the relevant portion of the input data stream, classifying and normalizing the bounded data, activating a relevant report template based on said identified latent information, populating said template with template-specified data, and processing the template-specified data to generate a report.

14 Claims, 6 Drawing Sheets

U.S. PATENT DOCUMENTS

| | | | |
|---|---|---|---|
| 6,182,029 | B1 | 1/2001 | Friedman |
| 6,192,112 | B1 | 2/2001 | Rapaport et al. |
| 6,289,353 | B1 | 9/2001 | Hazlehurst et al. |
| 6,292,771 | B1 | 9/2001 | Haug et al. |
| 6,347,329 | B1 | 2/2002 | Evans |
| 6,360,215 | B1 | 3/2002 | Judd et al. |
| 6,405,165 | B1 | 6/2002 | Blum et al. |
| 6,434,547 | B1 | 8/2002 | Mishelevich et al. |
| 6,438,533 | B1 | 8/2002 | Spackman et al. |
| 6,553,385 | B2 | 4/2003 | Johnson et al. |
| 6,854,086 | B2 | 2/2005 | Umen et al. |
| 6,915,254 | B1 | 7/2005 | Heinze et al. |
| 6,947,936 | B1 | 9/2005 | Suermondt et al. |
| 7,124,144 | B2 | 10/2006 | Christianson et al. |
| 2002/0007285 | A1 | 1/2002 | Rappaport |
| 2002/0095313 | A1 | 7/2002 | Haq |
| 2002/0143824 | A1 | 10/2002 | Lee et al. |
| 2002/0169764 | A1 | 11/2002 | Kincaid et al. |
| 2003/0046264 | A1* | 3/2003 | Kauffman ........................ 707/1 |
| 2003/0061201 | A1 | 3/2003 | Grefenstette et al. |
| 2003/0079186 | A1 | 4/2003 | Gondo et al. |
| 2003/0115080 | A1 | 6/2003 | Kasravi et al. |
| 2003/0208382 | A1 | 11/2003 | Westfall |
| 2003/0233345 | A1 | 12/2003 | Perisic et al. |
| 2004/0103075 | A1 | 5/2004 | Kim et al. |
| 2004/0139400 | A1 | 7/2004 | Allam et al. |
| 2004/0186746 | A1 | 9/2004 | Angst et al. |
| 2004/0186747 | A1* | 9/2004 | Nakano et al. .................... 705/3 |
| 2004/0205638 | A1 | 10/2004 | Thomas et al. |
| 2004/0220895 | A1 | 11/2004 | Carus et al. |
| 2004/0243545 | A1 | 12/2004 | Boone et al. |
| 2004/0243551 | A1 | 12/2004 | Boone et al. |
| 2004/0243552 | A1 | 12/2004 | Titemore et al. |
| 2004/0243614 | A1 | 12/2004 | Boone et al. |
| 2004/0249636 | A1* | 12/2004 | Applebaum et al. .......... 704/231 |
| 2005/0108010 | A1 | 5/2005 | Frankel et al. |
| 2005/0114122 | A1 | 5/2005 | Uhrbach et al. |
| 2005/0120020 | A1 | 6/2005 | Carus et al. |
| 2005/0120300 | A1 | 6/2005 | Schwager et al. |
| 2005/0144184 | A1 | 6/2005 | Carus et al. |

OTHER PUBLICATIONS

U.S. Appl. No. 10/953,471, filed Sep. 29, 2004, Cote et al.
U.S. Appl. No. 11/069,203, filed Feb. 28, 2005, Cote et al.
U.S. Appl. No. 11/007,626, filed Dec. 8, 2004, Cote et al.
U.S. Appl. No. 10/951,281, filed Sep. 27, 2004, Cote et al.
U.S. Appl. No. 10/953,448, filed Sep. 30, 2004, Carus.
U.S. Appl. No. 10/951,291, filed Sep. 27, 2004, Uhrbach.
U.S. Appl. No. 10/953,474, filed Sep. 29, 2004, Frankel.
U.S. Appl. No. 11/068,493, filed Feb. 28, 2005, Carus et al.
U.S. Appl. No. 10/787,889, filed Feb. 27, 2004, Carus.
U.S. Appl. No. 10/447,290, filed May 2, 2003, Boone.
U.S. Appl. No. 10/448,320, filed May 30, 2003, Boone.
U.S. Appl. No. 10/448,317, filed May 30, 2003, Boone.
U.S. Appl. No. 10/448,325, filed May 30, 2003, Titemore.
U.S. Appl. No. 10/413,405, filed Apr. 15, 2003, Carus.
U.S. Appl. No. 10/948,625, filed Sep. 23, 2004, Schwager.
Song et al., "A Graphical Interface to a Semantic Medical Information System", Journal of Foundations of Computing and Decision Sciences, 22(2), 1997.
Song et al., "A Cognitive Model for the Implementation of Medical Problem Lists, Proceedings of the First Congress on Computational Medicine", Public Health and Biotechnology, Austin, Texas, 1994.
Song et al., A Graphical Interface to a Semantic Medical Information System, Karp-95 Proceedings of the Second International Symposium on Knowledge Acquisition, Representation and Processing, pp. 107-109, 1995.
Epic Web Training Manual, pp. 1-33, 2002.
Hieb, Research Note, NLP Basics for Healthcare, Aug. 16, 2002.
Shalizi et al., "Pattern Discovery in Time Series, Part I: Theory, Algorithm, Analysis and Convergence", Journal of Medicine Leaning Research? (2002)?-? Submitted Oct. 28, 2002: Published ? 2002.
Nevill-Manning et al., "The Development of Holte's 1R Classifier", Department of Computer Science.
Cutting et al., A Practical Part-of-Speech, Xerox Palo Alto Research Center.
Zavrel et al., Recent Advance in Memory-Based Part-of-Speech Tagging, ILK/Computational Linguistics.
Brill, Some Advances in Transformation-Based Part-of-Speech Tagging, Spoken Language Systems Group.
Nivre, DAV723: Language Technology Finite State Morphology, Vaxjo University of Mathematics and Systems Engineering, p. 1-11.
Creutz, "Morphology and Finite-State Transducers", Oct. 31, 2001, Chapter 3, Jurafsky & Martin.
Http // www comp lancs ac uk/computing/research/stemming/general/index htm, printed Jul. 19, 2004.
http // www comp lancs ac uk/computing/research/stemming/general/stemmingerrors htm, printed Jul. 19, 2004.
http // www comp lancs ac uk/computing/research/stemming/general/performance htm, printed Jul. 19, 2004.
Lee et al., Cleaning Data for Mining and Warehousing, Lecture Notes in Computer Science vol. 1677 archive, Proceedings of the 10$^{th}$ International Conference on Database and Expert Systems Applications, pp. 751-760, Spinger-Verlag, London, 1999.
Van Rijsbergen, Information Retrival, 2$^{nd}$ Ed., Ch. 5, Butterworths, London, 1979.
Day, Extracting Knowledge from Text Using Learning by Constraint Relaxation (LCR), CSI, www csi-inc com/CSI/pdf/jday icim02 pdf.
Gale et al., "Discrimination Decisions for 100,000-Dimensional Spaces", Current Issues in Computational Linguistics, Kluwer Academic Publishers, pp. 429-450.
Daelemans, et al., TIMBL: Tiburg Memory Based Learner, Version 5,0, Reference Guide, ILK Research Group Technical Report Series No. 04-02 (ILK-0402), ILK Research Group, Tilbur University, Tilburg, Netherlands, 2004.
Case Study: Massachusetts Medical Society, http // www Microsoft com/resources/casesstudies/CaseStudy asp?caseStudyID=14931, posted Jan. 13, 2004.
Braithwaite, Continuity of Care Record (CCR), http // www h17 org/library/himss/2004Orlando/ContnuityofCareRecord pdf.
Wagemann, EHR vs. CCR: What is the Difference Between the Electronic Health Record and the Continuity of Care Record?, Medical Records Institute, 2004.
Press Release: Kryptiq Announces Support of CCR Initiative and Introduces New Solutions that Enable Information Portability, Accessibility and Clinical System Interoperability, http // www kryptiq com/News/PressRelease/27 html, posted Feb. 27, 2004.
Work Item Summary: WK4363 Standard Specification for the Continuity of Care Record (CCR), http // www astm org/cqi-bin/SoftCart exe/DATABASE.CART/WORKITEMS/WK4363htm?+mystore, Mar. 3, 2004.
Continuity of Care Record (CCR): The Concept Paper of the CCR v. 2.1b, http // www bhtinfo com/CCR Concept%20Paper. 1.5doc.
Continuity of Care Record, American Academy of Family Physicians, http // www aafp org/x24962.xml?printxml, posted Nov. 12, 2003.
Continuity of Care Record (CCR), AADP Center for Health Information Technology, http // www centerforhit or/x201 xml, posted Aug. 20, 2004.
Core Measures Web Page, Joint Commission on Accreditation of Healthcare Organizations, http // www icaho org/pms/core+measures, printed Mar. 22, 2004.
Specifications Manual for National Implementation of Hospital Core Measures, v.2.0, Joint Commission on Accreditation of Healthcare Organizations, http // www icaho or/pms/core+measures/information+on+final+specifications htm.
Code Information and Education Web Page, American Medical Association, http // www amassn org/ama/pub/category/3884 html, printed Mar. 22, 2004.
Category III CPT Codes, American Medical Association, http // www ama-assn org/ama/pub/article/3885-4897 html, printed Mar. 22, 2004.
ICD-9-CM Preface (FY04), http // ftp cdc gove/pub/health statistics/NCHS/publications/ICD9-cm/2004/prefac05 rtf.
ICD-9-CM Official Guidelines for Coding and Reporting, effective Oct. 1, 2003.

Yang et al,., "Faster Algorithm of String Comparison", Pattern Analysis and Applications, vol. 6, No. 1, Apr. 2003, pp. 122-133.

"Hardware Reference Manual", Release 3 for DOS, Revised Jan. 1994, PIKA Technologies, Inc., Ontario, Canada, available at, http // www pikatechnologies com/downloads/legacy/AVA%20B-Series%20Haredware%20Manual pdf, (last accessed Jul. 25, 2005).

Customizing D/41 Call Analysis:, date unknown, Intel Corp., Santa Clara, California, available at http // resource intel com/telecom/support/appnotes/custd41d htm, (last accessed Jul. 25, 2005).

International Search Report for PCT Application Serial No. PCT/US2004/016878, International Filing Date May 28, 2004.

Smith et al., "MICROARRAS: An Advanced Full-Text Retrieval and Analysis System", ACM 1987, p. 187-195.

* cited by examiner

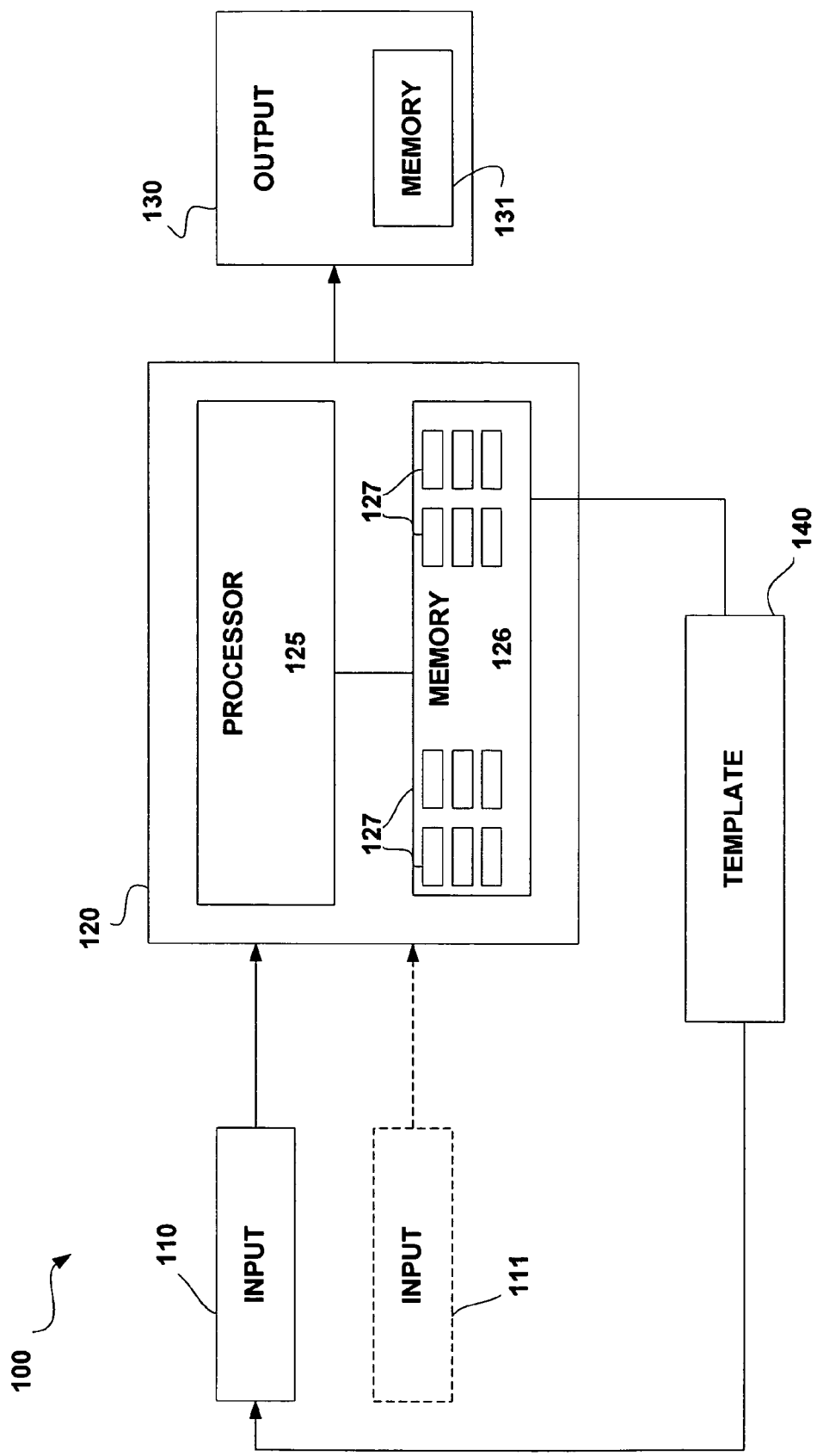

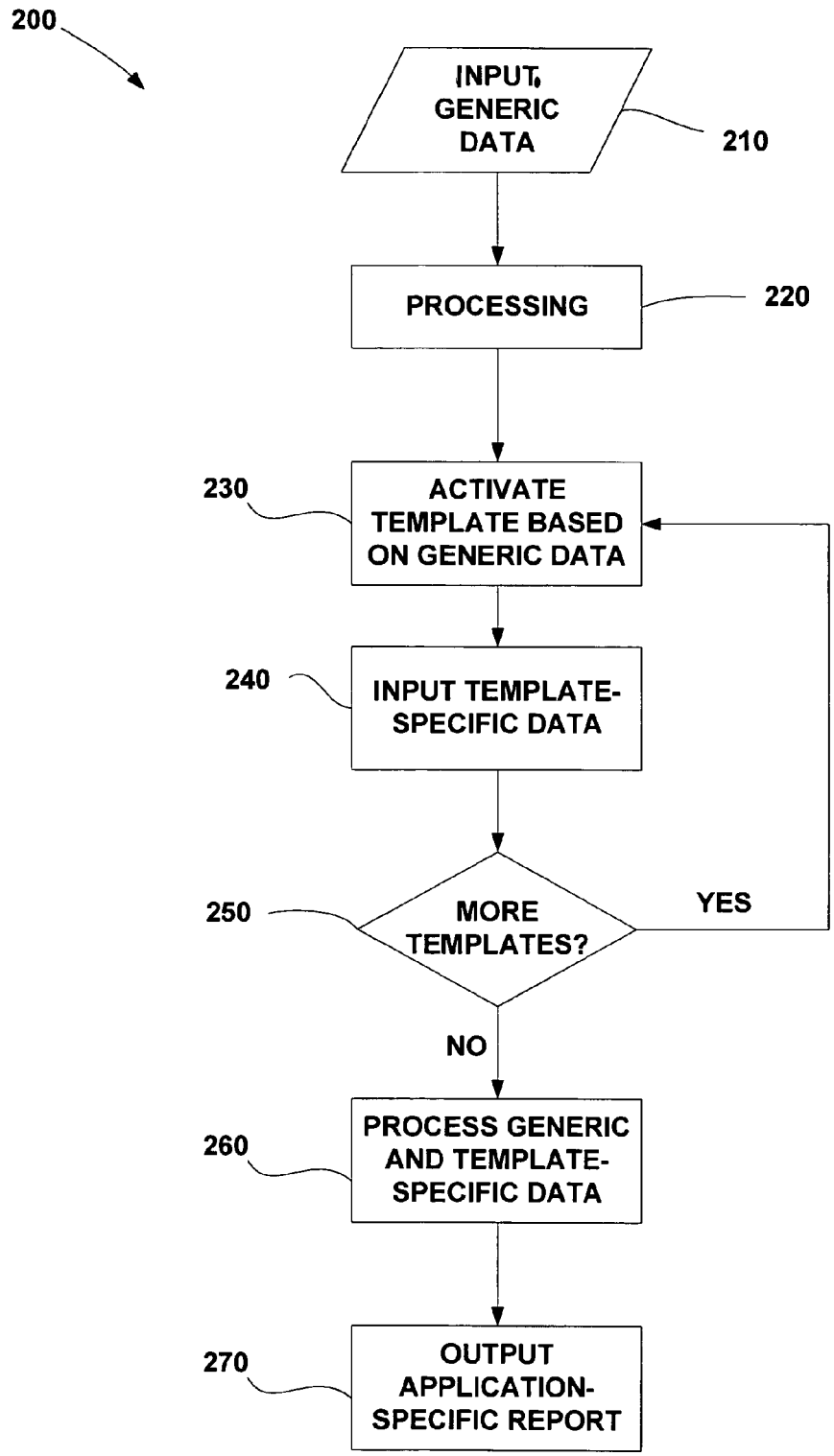

CATEGORIZATION OF INFORMATION USING NATURAL LANGUAGE PROCESSING AND PREDEFINED TEMPLATES

CROSS-REFERENCE TO RELATED APPLICATIONS

This application is a continuation of U.S. patent application Ser. No. 10/840,428, filed May 7, 2004 now U.S. Pat. No. 7,379,946, which claims priority to U.S. Provisional Application No. 60/557,834, filed Mar. 31, 2004, and entitled "CATEGORIZATION OF INFORMATION USING NATURAL LANGUAGE PROCESSING AND PREDEFINED TEMPLATES," which is hereby incorporated by reference in its entirety.

This application also relates to co-pending U.S. patent application Ser. No. 10/413,405, entitled, "INFORMATION CODING SYSTEM AND METHOD", filed Apr. 15, 2003; co-pending U.S. patent application Ser. No. 10/447,290, entitled, "SYSTEM AND METHOD FOR UTILIZING NATURAL LANGUAGE PATIENT RECORDS", filed on May 29, 2003; co-pending U.S. patent application Ser. No. 10/448,317, entitled, "METHOD, SYSTEM, AND APPARATUS FOR VALIDATION", filed on May 30, 2003; co-pending U.S. patent application Ser. No. 10/448,325, entitled, "METHOD, SYSTEM, AND APPARATUS FOR VIEWING DATA", filed on May 30, 2003; co-pending U.S. patent application Ser. No. 10/448,320, entitled, "METHOD, SYSTEM, AND APPARATUS FOR DATA REUSE", filed on May 30, 2003, co-pending U.S. Provisional Patent Application 60/507,136, entitled, "SYSTEM AND METHOD FOR DATA DOCUMENT SECTION SEGMENTATIONS", filed on Oct. 1, 2003; co-pending U.S. Provisional Patent Application 60/507,135, entitled, "SYSTEM AND METHOD FOR POST PROCESSING SPEECH RECOGNITION OUTPUT", filed on Oct. 1, 2003; co-pending U.S. Provisional Patent Application 60/507,134, entitled, "SYSTEM AND METHOD FOR MODIFYING A LANGUAGE MODEL AND POST-PROCESSOR INFORMATION", filed on Oct. 1, 2003; co-pending U.S. Provisional Patent Application 60/506,763, entitled, "SYSTEM AND METHOD FOR CUSTOMIZING SPEECH RECOGNITION INPUT AND OUTPUT", filed on Sep. 30, 2003, co-pending U.S. Provisional Patent Application 60/533,217, entitled "SYSTEM AND METHOD FOR ACCENTED MODIFICATION OF A LANGUAGE MODEL" filed on Dec. 31, 2003, co-pending U.S. Provisional Patent Application 60/547,801. entitled, "SYSTEM AND METHOD FOR GENERATING A PHRASE PRONUNCIATION", filed on Feb. 27, 2004, co-pending U.S. patent application Ser. No. 10/787,889 entitled, "METHOD AND APPARATUS FOR PREDICTION USING MINIMAL AFFIX PATTERNS", filed on Feb. 27, 2004; and co-pending U.S. Provisional Application No. 60/547,797, entitled "A SYSTEM AND METHOD FOR NORMALIZATION OF A STRING OF WORDS," filed Feb. 27, 2004, all of which co-pending applications are hereby incorporated by reference in their entirety.

FIELD OF THE INVENTION

The invention relates generally to methods and apparatus for categorizing input data in speech recognition systems and classifying the data into predetermined classifications. More particularly, the invention relates to methods and apparatus for categorizing input data by combining traditional data input methods, natural language processing techniques, and providing templates to users to provide additional data and facilitate extraction of data from free-form text based at least in part on the template.

BACKGROUND OF THE INVENTION

Traditionally, medical dictation systems allow physicians or other caregivers to dictate free-form speech that is later typed by a transcriptionist or transformed into written text by a computer using automated speech recognition (ASR). The resulting report may then be used to document an encounter with a patient and may subsequently be added to the patient's medical record. There have been a few attempts to construct natural language processing (NLP) software that may automatically extract key clinical information such as problems, medications, and procedures from medical reports. Extracting these data with a high degree of accuracy has proven to be a difficult task due to the complex nature of language, the many ways that a medical concept can be expressed, and the inherent complexity of the subject matter. As a result, NLP software tends to be large and complex, difficult to develop and maintain, and demands significant processing power, working memory, and time to run.

Because traditional systems are not fully capable of extracting all of the relevant information from, for example, a medical report, either because of system limitations or the failure of a medical professional to record the information, Health Information Management (HIM) personnel often spend a significant amount of time compiling data for back-end reporting purposes. Back-end reporting may be required for tasks such as compliance, accreditation with a standards body, government/Medicare reporting, and billing. These data are usually gathered manually by individuals who must read through all supporting documentation in a patient's file and then enter the data in a paper form or into a software package or database.

Practitioners in the medical field are faced with other problems that may adversely affect their ability to properly record and catalog relevant data. One such problem is that some of the data that needs to be collected for record-keeping purposes does not necessarily come up in ordinary patient-physician interaction. Additionally, at least in the medical field, there are a number of different purposes for which records may be kept, such as, for example, the ORYX quality reporting initiative that the Joint Commission on the Accreditation of Healthcare Organizations (JCAHO) has incorporated into its accreditation process for hospitals, CPT-4 (Current Procedural Terminology-4$^{th}$ Edition) billing codes, ICD-9-CM (International Classification of Diseases-9$^{th}$ Revision-Clinical Modification), and Medicare E&M (Evaluation and Management) codes. Due to the number of potential uses of medical reports and the corresponding medical information fields that may need to bee filled, it may be difficult for a physician to remember to include all of the relevant information for each of these predetermined categorization schemes.

A first predetermined categorization scheme may include the ORYX quality-reporting initiative that has been incorporated into the hospital accreditation process by JCAHO. The ORYX initiative identifies a number of core measures that would be used to evaluate a hospital's performance. These may include core measure sets for the following conditions: (1) acute myocardial infarction (AMI); (2) heart failure (HF); (3) community acquired pneumonia (CAP); and (4) pregnancy-related conditions. Other core measure sets may include surgical infection prevention (SIP).

The JCAHO estimates that the collection of data related only to the AMI and HF core measures, assuming an average number of cases of AMI at 28 and the number of HF cases to be 40 per month, was 27.4 hours a month. Some of the information that may be sought may be obscure and therefore may not come up in ordinary conversation. Therefore, some of the information may be lost completely when physicians or other health-care professionals dictate their interviews and related treatments related to their patients. For example, as of Jul. 1, 2002, the core measures related to AMI included: (1) whether aspirin was administered upon admission; (2) whether aspirin was administered on discharge; (3) was angiotensin converting enzyme inhibitor (ACEI) used on patients exhibiting anterior infarctions or a left ventricular ejection fraction (LVEF); (4) was the patient counseled to stop smoking; (5) was a beta blocker prescribed at discharge; (6) was a beta blocker prescribed at arrival; (7) time to thrombolysis (the administration of an enzyme configured to break down a blood clot); (8) time to percutaneous transluminal coronary angioplasty (PTCA); and (8) inpatient mortality.

A second predetermined categorization scheme may include the IDC-9-CM classification. This classification is intended to facilitate the coding and identifying the relative incidence of diseases. The ICD-9-CM is recommended of use in all clinical settings and is, along with CPT-4, the basis for medical reimbursements, but is required for reporting diagnoses and diseases to all U.S. Public Health Service and Centers for Medicare & Medicaid Services. Therefore, the importance of maintaining accurate records for this type of reporting is apparent.

A third example of a predetermined categorization scheme may include the Current Procedural Terminology, Fourth Edition (CPT-4), which is a listing of descriptive terms and identifying codes for reporting medical services and procedures. The purpose of the CPT listings is to provide a uniform language that accurately describes medical, surgical, and diagnostic services, and thereby serves as an effective means for reliable nationwide communication among physicians, patients, and third parties. As noted above, CPT-4 is, along with ICD-9-CM, the basis for medical reimbursements for procedures.

A fourth example of a predetermined categorization scheme may include the Medicare Evaluation and Management (E&M) codes. To determine the appropriate E&M code, physicians may, in some circumstances, be required to make judgments about the patient's condition for one or more key elements of service. These key elements of service may include, for example. patient history, examination, and medical decision-making. Additionally, the physician may, in some situations, be required to make a judgment call regarding the nature and extent of the services rendered by the physician. For example, when a cardiologist sees a new patient for cardiology consultation in, for example, an outpatient clinic setting, to bill for this encounter, the cardiologist may have to select between a number of predetermined billing codes. For example, the physician may select E&M codes from category 99241 to 99245. and then may select the appropriate service from one of the category's five E&M levels. Inaccurate determination of these levels, either down-coding (by providing a code below the appropriate level and thereby billing at an inappropriately low level) or up-coding (by providing a code above the appropriate level and thereby billing at an inappropriately high level), may result in financial penalties, which in some instances may be severe. These four exemplary systems for identifying and coding medical problems, procedures, and medications provide the user of the particular coding system with a different informational structure. For example, the JCAHO ORYX information structure used for reporting for accreditation of a hospital to the JCAHO, will likely be different from the information structure required for submissions to the Centers for Medicare & Medicaid Services for, for example, Medicare reimbursement, which will have a different informational structure than that required for ICD-9-CM, CPT-4, and E&M billing.

As mentioned above, when dictating patient reports, physicians may fail to document key pieces of data which are required for these back-end reporting processes, requiring the individuals responsible for the back-end reporting processes to either get the information from some other source, go back to the physician and request the required information, or go without the information, leaving a gap in their data set. This results in reduced efficiency, increased expenses and time-on-Task, and also contributes to increased error and omission rates.

As can be seen by the foregoing, the process of recording and entering medical information may be very costly, and despite the costs, data may still be incomplete. Current natural language processing implementations that work from free-form text ("non-bounded" input data or text) require complex data- and processing-intensive techniques that are not always consistent, accurate, and comprehensive. Therefore, what is needed is a simplified method and apparatus for identifying terms of art within a stream of input data, such as, for example, medical terms and classifying the terms. Additionally, there is a need for a classification system that may provide the user with both prompts or reminders to collect certain predetermined information and assistance in collecting and classifying these terms.

SUMMARY OF THE INVENTION

In light of the above-identified deficiencies of contemporary methods and systems, it is thus an object of the present invention to provide a system and method for collecting, classifying, and normalizing input data by combining traditional data input methods, natural language processing techniques, and providing templates to users associated with a predetermined classification scheme based on the input normalized data. Traditional input methods may include methods such as, for example, those used in database applications involving fielded input forms consisting of input fields, check boxes, radio buttons, text boxes, and other graphical input objects; and sequences of such forms following a specified workflow pattern.

In a first aspect, the present invention may include a method including receiving an input stream of data and processing the input stream of data. The input stream of data may include latent information. This latent information may be identified by processing the input data. A template associated with the identified latent information may be activated. Based on this template, template-specific data may be received. After receiving both the input stream of data and the template-specific data, this information can be processed to generate a report based on the input data and the template specific data.

Additional embodiments of the present invention may include receiving medical data. In other embodiments, the medical data may include data associated with medical problems, medications, allergies, or medical procedures. A report may be generated, and that report may be, for example, a JCAFHO ORYX report or alternatively an ICD-9-CM-CPT-4-, or E&M-based report. The report may include, for example, any type of billing report. In yet other embodiments, relevant portions of the input data stream may be identified and bounded. Subsequently, the bounded data may be classified and normalized. In another embodiment, processing may include, for example, classification, normalization, validation, and/or extraction. In yet another embodiment, activating a template may include selecting a template from a predetermined group of templates and activating the selected template.

In a second aspect, the invention may include a method of receiving and classifying information in a constrained data input scheme. The method may include inputting generic data including latent information. A template associated with that data category may be retrieved. Template-specific data may be processed along with the generic data to generate a report based on the generic data and the template-specific data.

In one embodiment, the generic data may include medical data. In yet another embodiment, the medical data may include, for example, at least one of a medical problem, a medication, an allergy, and a medical procedure. In an alternative embodiment, a report may include one of an accreditation report and a billing report. This report may be generated based on, for example, the template-specific data and the generic data. In yet another embodiment, processing of the generic data may include identification of the relevant portion of the input data stream, where the relevant portion of the data stream is associated with the latent information. Processing may also include performing at least one of a classification, a normalization, a validation, and an extraction process. In yet another embodiment, a method according to the invention may include identifying a relevant portion of the generic data, bounding the relevant portion of the generic data, identifying the latent information, and classifying and normalizing the relevant portion of the generic data.

In yet other embodiments of the present invention, activating a template may include selecting a template from a predetermined group of templates and activating the selected templates. In another embodiment, the latent information may be associated with a predetermined classification of information. The predetermined classification of information may only be one classification of a number of different classifications of information. The template activated in the activating step may be associated with the predetermined classification of information.

In a third aspect, the present invention may include processor-readable code stored on a processor-readable medium. The processor-readable medium may include code to receive generic data. This genetic data may include latent information. The processor-readable medium may include code to activate a template associated with the latent information, the template being associated with the predetermined category of information. The processor-readable medium may also include code for receiving template-specific data associated with the activated template, and may include code to process the generic data and template-specific data to generate a report or other structured or machine-readable outputs based on the generic data and the template specific data.

In other embodiments, the processor-readable medium may include code to receive medical data. In another embodiment, the computer-readable medium may include code to receive medical problem data, medication data, allergy data, and/or medical procedure data. In yet another embodiment of the invention, the code may include code to generate one or both of an accreditation report and a billing report based on the processed generic and template-specific data. In an alternative embodiment, the code may include code to identify a relevant portion of the generic data, the relevant portion of the generic data being associated with a predetermined class of information and may also include code to normalize the generic data. According to yet another embodiment of the invention, the code can include code to identify a relevant portion of the generic data, including the latent information, bound the relevant portion of the generic data, identify the latent information, and classify and normalize the relevant portion of the generic data.

BRIEF DESCRIPTION OF THE DRAWINGS

While the specification concludes with claims particularly pointing out and distinctly claiming the invention, it is believed the same will be better understood from the following description taken in conjunction with the accompanying drawings, which illustrate, in a non-limiting fashion, the best mode presently contemplated for carrying out the present invention, and in which like reference numerals designate like parts throughout the Figures wherein:

FIG. 1 shows a system architecture according to one embodiment of the invention;

FIG. 2 shows a logic flow diagram according to one embodiment of the present invention;

DETAILED DESCRIPTION OF THE PREFERRED EMBODIMENTS

Figure 3A:
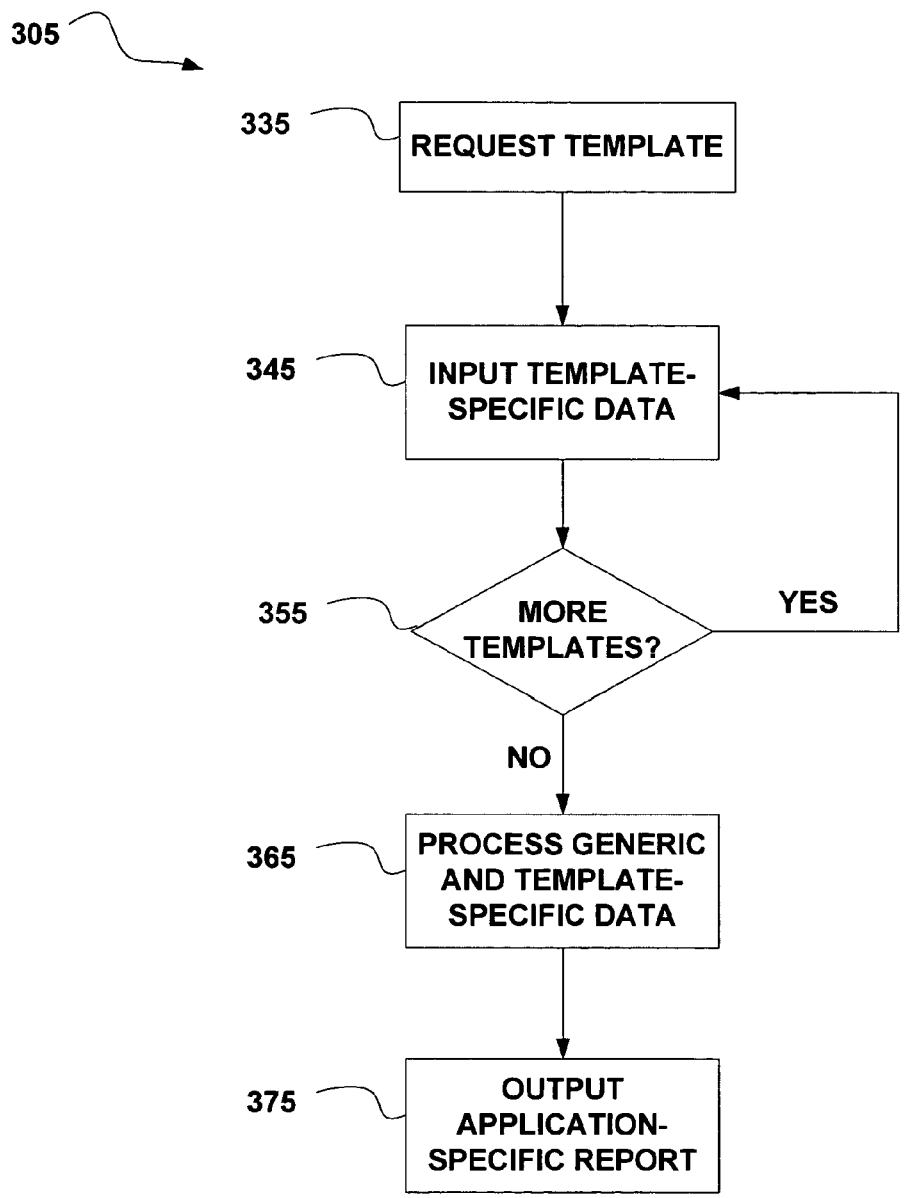
FIG. 3A shows a logic flow diagram according to one embodiment of the present invention.

The present disclosure will now be described more fully with reference to the Figures in which embodiments of the present inventions are shown. The subject matter of this disclosure may, however, be embodied in any different forms and should not be construed as being limited to the embodiments set forth herein.

FIG. 1 shows a system architecture according to one embodiment of the invention. The system may include a first input 110, and optionally may include a second input 111. The first input 110 may be, for example, a microphone for receiving voice signals and converting these signals into a data stream associated with recorded speech. Optionally, the second input 111 may include, for example, a stylus and a touch screen, a button, a computer mouse, a keyboard, or other input device. The specific form of input devices 110, 111 are not critical, so long as they permit data to be entered by a user. The first input 110 and the second input 111 can be coupled to a processing device 120. Processing device 120 can include a processor 125 and a memory 126. Memory may be configured to store a number of templates 127. The processing device 120 may be coupled to an output 130, which may include a memory 131.

When a user, such as, for example, a physician, dictates information into, for example, a first input 110, the speech may be converted into an analog or digital input data stream. This input data stream may be input into the processing device 120. Processing device 120 may be configured to process the input data stream. In one embodiment, the input data can include generic data. Generic data may be, for example, a typical conversation between a patient and the physician. The generic data may include data associated with comments about, for example, how the patient's son's baseball team is doing. Generic information may be any type of information, and is not limited to medical information, while medical information may be a particular subset of the generic data.

Generic data may include, for example, latent information. This latent information may be associated with a predetermined classification of information. The latent information may be, for example. information relating to a particular medical problem. Alternatively, latent information may be, for example, information related to an allergy, a treatment, or a medication.

The input data stream may be input into a processor 125. In one embodiment, the processor 125 may be configured to process the received input data stream using, for example, lightweight natural language processing. Lightweight natural language processing may be different from typical natural language processing in that for lightweight natural language processing, the processor need not determine what type of a term or phrase a word or sequence of words is and need not bound the word or sequence of words, but rather may rely on one or more templates to bound the word or sequence of words and determine what type of a term or phrase a word or sequence of words is. An additional embodiment of the present invention may incorporate natural language processing techniques such as, for example, text classification to determine which class of a number of predetermined templates are associated with a given input text.

For example, when an input data stream is processed, a template may be retrieved based on characteristics of the latent data within the data stream. A template 140 from a number of different templates 127 may be retrieved from memory and presented to, for example a user. The user may use this template 140 to input additional data, i.e., template-specific data into the processing device 120. In one embodiment, the template-specific data may be associated with a JCAHO core measure. In an alternative embodiment, the template-specific information may be associated with an ICD-9-CM code. In yet another embodiment, the template-specific information may be associated with a CPT-4 code. In yet another embodiment, the template-specific information may be associated with a billing requirement, using, for example CPT-4 medical terminology. In yet another embodiment, the template-specific information may be associated with an E&M code. In another alternative embodiment, the template-specific information may be associated with a user-defined template. The user defined template may include fields that a particular institution, such as, for example, a hospital, or a lab uses to maintain their own records.

When the template-specific and the generic information are further processed, using, for example, lightweight natural language processing, this information may be categorized, normalized, and organized to generate a specific report or a number of different reports or other structured or machine-readable outputs. These different outputs can be, for example, a surgery billing report using the CPT-4 coding scheme, a hospital insurance billing form using the ICD-9-CM coding scheme, a Medicare form using E&M codes, and a JCAHO ORYX coding and reporting scheme used to obtain and maintain accreditation for a particular hospital. The processed information may be sent to an output 130 where the information may be placed into such reports. These reports may be stored, for example, in memory 131, or alternatively, they may be printed out in hard copy, transmitted to a remote location, or any combination of these three outputs. Other outputs are also possible. For example, the reports and associated extracted information may be transferred to an external system such as. for example. clinical data repository (CDR) and/or an electronic medical record (EMR).

FIG. 2 shows a logic flow diagram according to an embodiment of the invention. As illustrated in FIG. 2, a method of categorizing information 200 in a constrained data input system may include inputting generic data, step 210. As discussed above, generic data may include all data that is recorded via dictation or other information recordation means. After inputting this data, the data may be processed, step 220. In one embodiment, the generic data may be processed using, for example, natural language processing (NLP). As discussed above, natural language processing may include at least two general steps. The first step is the identification of a relevant portion of the generic data. The relevant portion of the generic data may include latent information. This process may provide boundaries around the relevant data (i.e., the process may bound the relevant data), thereby allowing the program to recognize the latent information in a meaningful way. The second step may include the classification of the relevant portion of the data.

Once the generic data has been processed, step 220, a template may be activated based on the processed generic data, step 230. A template may be requested, step 230 based on the classification of the relevant portion of the data. In one embodiment of the invention, the template may be requested manually. The manual request for the template may include obtaining a list of relevant templates and selecting from the list of relevant templates at least one template that the user may be required to fill. In an alternative embodiment, the user may select the templates using, for example, a stylus on a touch pad screen. In yet another embodiment, the user may select the templates using, for example, a computer mouse or other computer peripheral. Once the template has been retrieved, the template may be presented to a user, such as, for example, a physician. The template may be presented to the user via any acceptable user-cognizable means, such as, for example, via audio, computer display, hard copy, or any other suitable output that is perceptible to a user.

Once receiving the template based on the input generic data has been completed, the user may input template-specific data into the system, step 240. This template specific-data may include, for example, data associated with a JCAHO core measure. For example, generic data may include the fact that a particular patient is over eighteen years old and that they are going to have a particular surgical procedure performed. In this example, the latent information may include, for example, the identification of the surgical procedure. However, the JCAHO protocol may require information regarding whether there was an infection related to the surgical procedure. Performance measures that are currently associated with this core measure include admission date, date of birth, ICD-9-CM principal procedure code, ICD-9-CM other procedure code, ICD-9-CM principal diagnosis code, admission diagnosis, surgery performed during stay, and infection prior to anesthesia. In one example, the physician may have input or have requested from a hospital information system generic data that may include the patient's name, patient's date of birth, date of admission, an admission diagnosis, and the fact that a particular surgical procedure may be required. Based on this information, and using, for example, natural language processing, the processor can access the appropriate JCAIIO-based template to remind the physician that additional data (i.e., ICD-9-CM other procedure code, ICD-9-CM principal diagnosis code, admission diagnosis, surgery performed during stay, and infection prior to anesthesia) may be required. This example is overly simplistic, as JCAHO requirements for record keeping related to core measures are well defined, and highly particularized; however, this example facilitates understanding of the invention in a broad sense. For more information relating to JCAHO reporting requirements, see "Specification Manual for National Implementation of Hospital Core Measures Version 2.0," which is hereby incorporated by reference in its entirety. By prompting the physician to record this additional information, the record associated with that patient's visit may be kept more accurately and more completely.

In one embodiment, a user may continue to input data into the system, and the categorization and processing system may be reviewing additional portions of generic data contemporaneously to determine if there are any more templates that need to be presented to the physician or other medical practitioner, step 250. In one embodiment, the medical practitioner may make this decision manually. If the user knows that there are additional templates required for submission for, for example, Medicare, they can retrieve this template from a list of templates associated with the input generic data. If there are additional templates that need to be presented to the user, they may be presented to the user so that the user may input additional template-specific information associated with the additional template. Once all relevant templates have been presented to the user, additional processing of the input generic data and the template-specific data may be performed, step 250. This additional processing may include entering data from the generic data and the template-specific data into, for example, fields in predefined databases. Template-specific information may be processed using, for example, lightweight natural language processing. The use of the lightweight (as opposed to heavyweight) natural language processing may be facilitated by the use of the templates. In an alternative embodiment, additional processing may include updating a patient record, such as, for example, a natural language patient record (NLPR). Examples of NLPRs are disclosed in co-pending U.S. patent application Ser. No. 10/413,405, entitled, "INFORMATION CODING SYSTEM AND METHOD", filed Apr. 15, 2003; co-pending U.S. patent application Ser. No. 10/447,290, entitled, "SYSTEM AND METHOD FOR UTILIZING NATURAL LANGUAGE PATENT RECORDS", filed on May 29, 2003, both of which are hereby incorporated by their reference in their entirety.

After processing the generic data and the template-specific data, step 260, an application-specific report or other structured or machine-readable outputs may be output, step 270. The outputs may be output in a number of different ways, including, for example, via an e-mail or other electronic information transmitting means, such as an encrypted data transmission line, hard-copy output. such as a print out, on a disk or other electronic or magnetic storage means. Other known outputs may be used to output the application-specific report or reports, step 27 (i. In one embodiment, the report may include an accreditation report, such as, for example, a JLA1-IU report. Alternatively, the report may be, for example, a billing report, such as, for example, a report using E&M codes, CPT-4 codes, ICD-9 or any other suitable billing codes.

FIG. 3A shows a logic flow diagram according to one embodiment of the invention. A method of entering data in a constrained data input task 305 may include requesting a template, step 335. Based on the requested template, the user may input template-specific data, step 345. In one embodiment, the user may need to request more than one template in step 335, and therefore, additional template-specific data may be input, step 345, based on a determination that the user had requested more than one template, step 355. In one exemplary embodiment of the invention, the user may make this determination manually. In an alternative embodiment, the logic in, for example, a computer software program may be configured to store and recall the number of templates that the user had selected.

After a determination has been made that the user has addressed all of the templates, and all of the template-specific data has been received, generic data and the template specific data may be further processed, step 365, using, for example, some form of natural language processing. Processing may include, for example, converting dictated speech into text, and then placing relevant text into specific portions of a document. Thus, latent information may be placed into predetermined locations within a document, such as, for example, a natural language patient record (NLPR), based on latent information. Latent information may be identified by looking to, for example, either form or content of the input data. In one embodiment, the natural language processing may include lightweight natural language processing. The use of lightweight natural language processing may be facilitated by the use of the templates. Additional processing may include, for example, normalization, validation, and extraction of relevant data. Any one of these processes may be used either along or in combination with other processing functions. Validation may include, for example, receiving template-specific data and generic data. This data may be compared to a pre-existing set of facts that have been confirmed. After the generic data and the template-specific data have been compared to the confirmed data set, the data may then be stored in a superset document based on the comparison and the confirmed fact or facts. Additional examples of validation are disclosed in, for example, co-pending U.S. patent application Ser. No. 10/448, 317, entitled, "METHOD, SYSTEM, AND APPARATUS FOR VALIDATION", filed on May 30, 2003, which is hereby incorporated by reference in its entirety. In one embodiment, generic data may include, for example, any form of data that may be associated with a natural language patient record (NLPR). In yet another embodiment, generic data may include any type of information received during a patient encounter.

After the generic data and the template-specific data are further processed, step 365. an application-specific report or other structured or machine-readable outputs may be generated using the processed generic and template-specific data, step 375. The output may be, an accreditation report, such as, for example, a JCAHO-specific report associated with one of the JCAHO core measures. Alternatively, the report may be a billing report, such as, for example, a Medicare-specific report. Any type of report may be generated based on the type of data input as well as the predefined template utilized by the user.

In one embodiment, the template may be requested manually using, for example, a pull-down menu in a graphical user interface (GUI) to select the template based on an anticipated encounter. For example, if a physician determines that a particular patient may have community acquired pneumonia (CAP), a JCAHO core measure, the physician may call-up a predefined dictation template associated with CAP and may enter the relevant information for reporting to JCAHO. By using the predefined dictation template, the physician may be assured that all of the relevant data required by JCAHO has been entered into the patient's record. In yet another embodiment, the physician may retrieve a hard copy of the dictation template to assist them with the input of template-specific information.

Figure 3B:
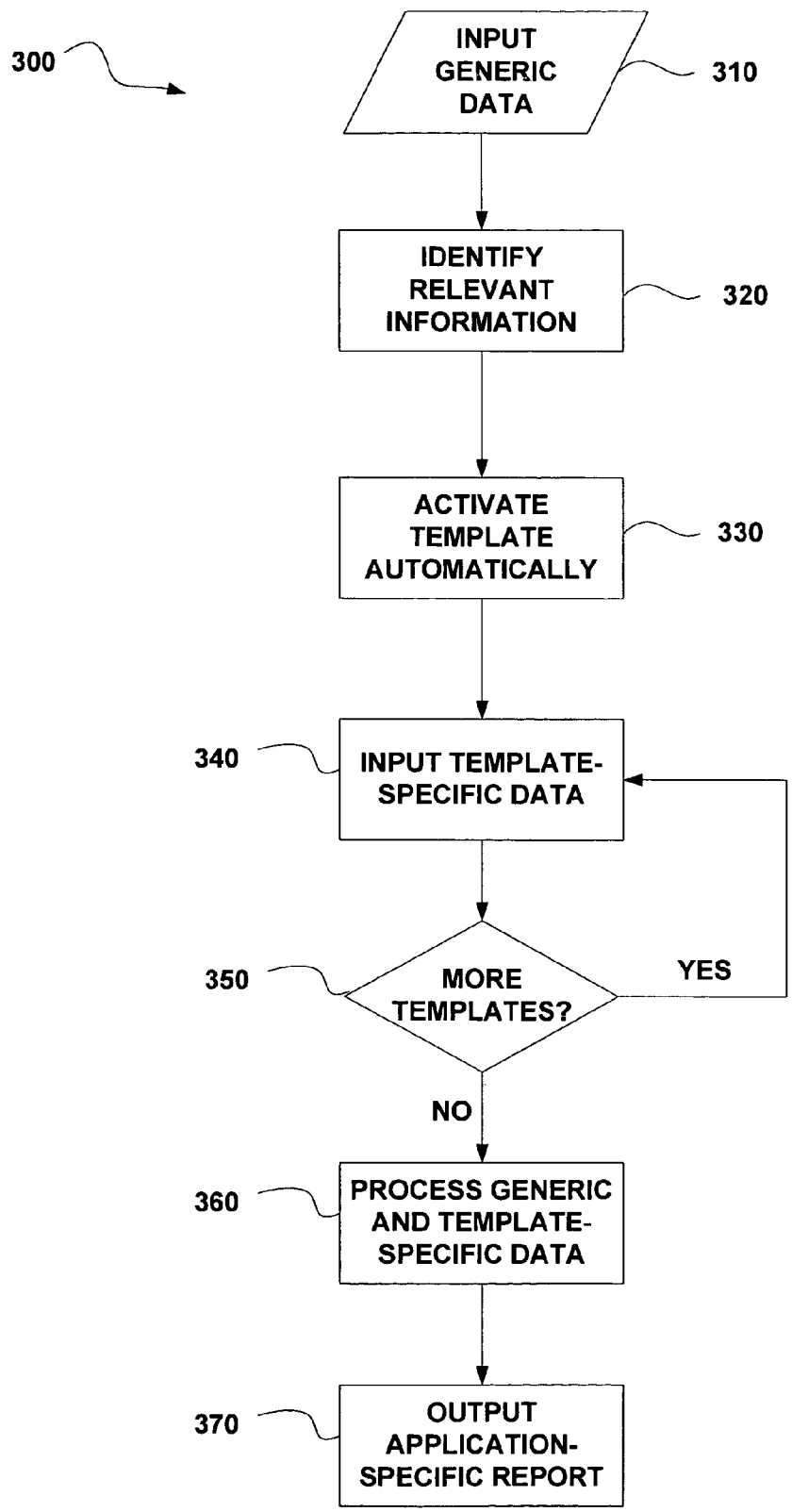
FIG. 3B shows a logic flow diagram according to another embodiment of the present invention.

FIG. 3B shows a logic flow diagram according to another embodiment of the invention. The method of classifying data 300 illustrated in FIG. 3B is similar to that illustrated in FIG. 2. Geneic data may be input into the data classification system, step 310. The system, using, for example, heavy-weight natural language processing (processing that may require sophisticated techniques to bound and classify free-form text, but may proceed directly with classification and normalization within typically constrained target domains), may identify the relevant portion or portions of the generic data input into the system, step 320. These relevant portions of the generic data may include latent information. As described above, in an alternative embodiment, the identification of relevant information may be performed using heavyweight natural language processing.

Based on the relevant data identified and tagged by heavyweight natural language processing, a template may be activated based on the identification of the relevant predetermined categories of information, step 330. In one embodiment, all relevant templates may be activated and the user may selectively input template-specific data associated with each template of the activated templates. In an alternative embodiment, a list including all relevant templates may be presented to a user in, for example, a graphical user interface (GUI). In one embodiment, the templates can be retrieved automatically, step 330, without any further input from the user. The automatic retrieval of templates, step 330, may be based on the identification of relevant information, step 320, using, for example, natural language professing. In one embodiment, software for performing this method may automatically run through all of the templates activated. In one embodiment, software for performing the activation of the templates may be configured to score or process the templates and may present the templates that exceed a predetermined score or that are identified by rules or conventions to the user. The automatic identification and retrieval of relevant templates may save the user time and effort determining which templates are required for a particular interaction with, for example, a patient.

In yet another embodiment, a system administrator may maintain a list of including a multitude of different templates and may manage the templates. Management of the templates may included, for example, adding additional fields to a particular template, removal of fields from a template, defining the possible values or ranges of values of fields, adding new templates, restricting access to particular templates, and removing templates. This is advantageous in that only the templates that are used, for example, by the hospital or clinic, may be accessed in determining the relevant templates to retrieve. For example, the systems administrator may receive instructions that the institution would like to begin keeping track of a particular type of information about their patients or clients. The system administrator may construct a new template that prompts the user for the submission of the relevant information.

Once the relevant template or templates have been activated, the user may input template-specific information associated with the particular template, step 340. A determination may then be made to see if all of the activated templates have been used, 350. Any known scoring or rule-based method may be used in connection with the scoring or processing of the templates based on the input generic data. If a determination has been made that there are no more activated templates, the input generic data and the template-specific data can be processed, step 360. In one embodiment, additional processing may include entering data from the generic data and the template-specific data into, for example, fields in predefined databases or documents. Alternatively or in addition to the aforementioned embodiments, processing step 360 may include, for example, a classification process, a normalization process, a validation process, and/or an extraction process.

These predefined databases including the processed generic data and the template-specific data can be used to generate reports, step 370, as described above with reference to FIG. 3A. Exemplary reports have been described above with reference to FIG. 2, and may include, for example, billing reports, medicare reports, JCAHO accreditation reports. Additionally, user-defined reports may also be generated. In one embodiment. the type of report may be associated with the templates activated in step 330.

In other alternative embodiments, the system and method may include a means for retrieving information that may have been input from previous encounters and utilizing this information when determining which templates to retrieve. For example, the system may include software code to access a natural language patient record (NLPR) and retrieve information received in connection with previous encounters. This information can be combined with the generic data received in either of steps 210 or 310 in determining which templates should be retrieved. If all of the relevant information required for a particular template has been received, then that particular template need not be returned. In an alternative embodiment, the template may be returned to the user with an indication that the information contained therein is complete. This may allow the user to double-check information that was entered in the past for accuracy.

Figure 4:
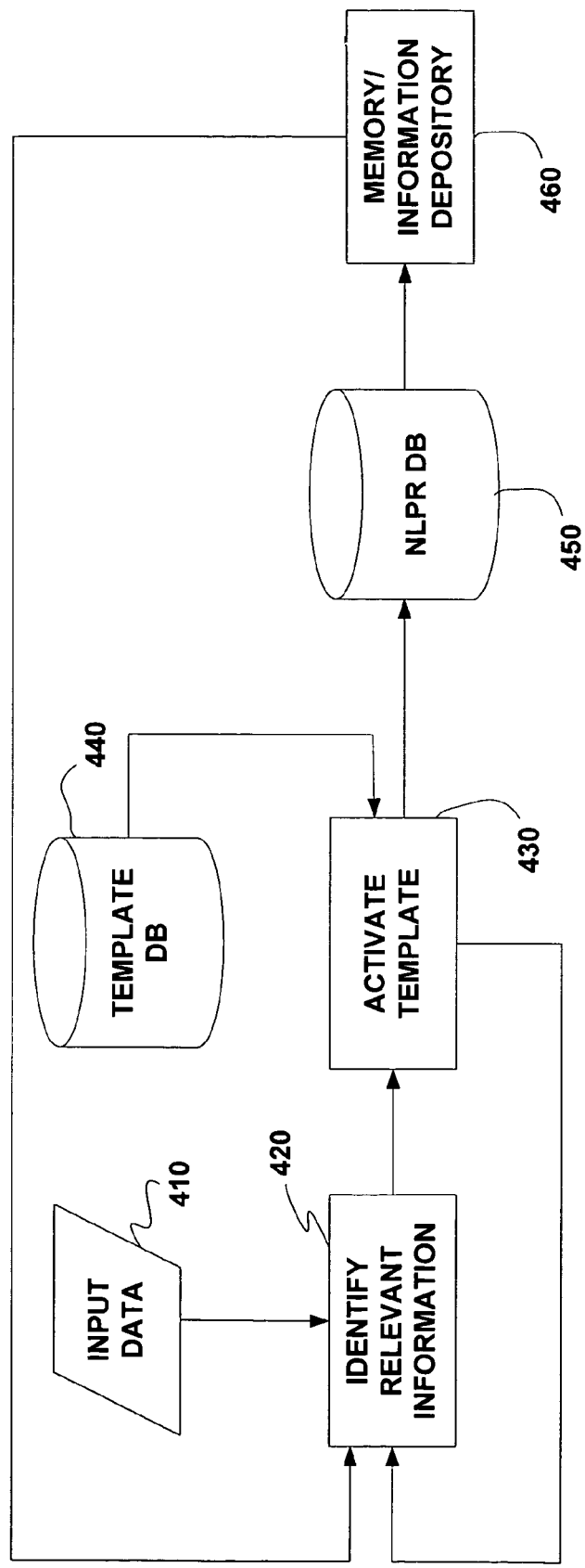
FIG. 4 shows a logic flow diagram according to another embodiment of the present invention.

FIG. 4 shows a logic flow diagram according to another embodiment of the invention. The data categorization scheme illustrated in FIG. 4 may be used to receive and categorize and normalize data for, for example, constrained data input tasks. In one process according to an embodiment of the intention, data may be input, step 410. This data may be generic data. The input data may be fed into a processor that can bound the relevant data from the input data. Relevant information may include, for example, latent information. At least one template may be retrieved from the template database 440 based on the relevant information, step 430. In one embodiment, a billing template may be retrieved after each patient encounter to remind the physician to bill for the encounter appropriately. After the relevant template has been retrieved, additional data may be input by the user and the data can be used to update, for example, a natural language patient record. This natural language patient record may be stored, for example, in a NLPR database, 450. The NLPR database 450 may be stored on, for example, a hard drive. Alternatively, the NLPR database may be stored on a server that may be accessed by a number of different end-users. The NLPR database may be stored on any accessible medium.

After the NLPR database 450 has been updated, the template-specific information and the generic information may be sent to a memory or other information depository 460. In one embodiment, this information can include user preferences, which may permit the association of a particular word or string of words with a particular classification or category of information. In this manner the system may include a feedback system, as illustrated in FIG. 4 that may permit the system to learn particular word associations thereby facilitating quicker processing of information. For example, if a user calls a particular term, such as, for example, acetaminophen by the name aspirin, and the system did not recognize or associate acetaminophen with aspirin, the user can instruct the system to make this association so that the next time that the term acetaminophen is input with the generic data, the system will recognize this term as being associated with aspirin and will collect and retrieve all relevant templates associated with aspirin that may be required in the particular context. While this example is relatively simplistic and the base system may already include the association of acetaminophen with aspirin, it illustrates the adaptability of the system to different users and different terminology that may occur due to demographics, education, or other variables that may cause the form of a particular term to differ.

Figure 5:
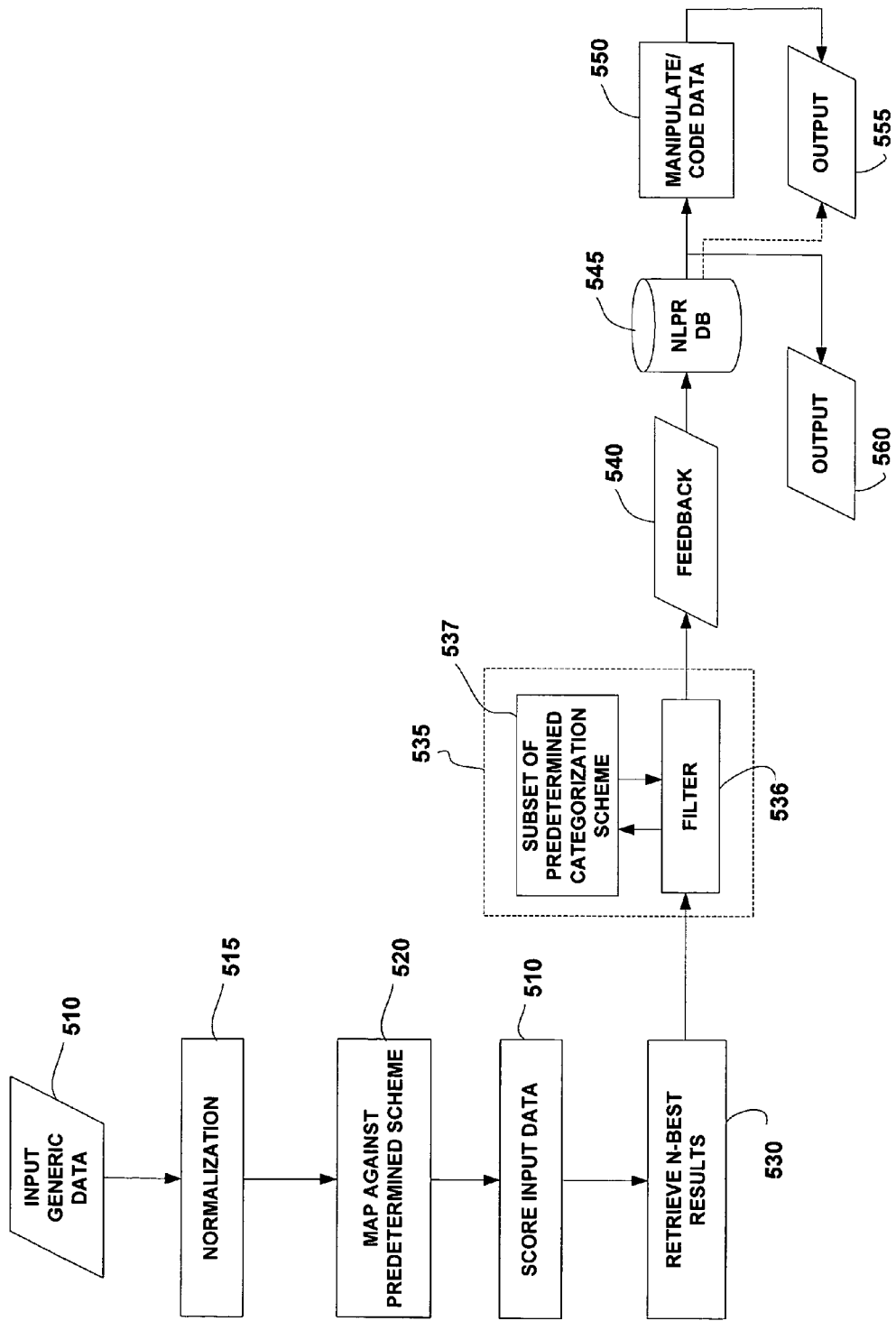
FIG. 5 shows a logic flow diagram according to yet another embodiment of the present invention.

FIG. 5 shows a logic flow diagram according to yet another embodiment of the invention. As illustrated in FIG. 5 a method of categorizing data according to another embodiment of the invention can include inputting generic data, step 510. This generic data can include all types of data including data associated with discussions unrelated to medical treatment, but may include data associated with, for example, medical problems, medical procedures, allergies, and medication, or any combination of this information. Once the generic data has been input, 510, the generic data can be normalized, step 515. In one embodiment, the information can be normalized to the SNOMED CT ontology. Exemplary methods and systems for performing this normalization are described in detail in U.S. Provisional Application No. 60/547,797, entitled "A SYSTEM AND METHOD FOR NORMALIZATION OF A STRING OF WORDS," filed Feb. 27, 2004, which is hereby incorporated by reference in its entirety. Other methods of normalization may be used to perform normalization step 515, as will be appreciated by one skilled in the art. Normalization of the input generic data may permit the system to put input data in a more easily recognizable form for comparison with various databases. In one embodiment normalization may permit the identification and tagging of relevant information. Once the generic data has been normalized, step 515, the information may be mapped against a predetermined classification scheme, step 520. Terms within the normalized data may be compared against the predetermined classification scheme. Classifications within the predetermined classification scheme may be associated with a number of terms. These terms may be the normalized form of particular medical terminology. In one embodiment, each predetermined classification or categorization may be associated with one or more medical terms normalized in accordance with, for example, the SNOMED CT Medical Nomenclature or a Clinical Subset of this nomenclature.

In one embodiment, a classification for relevant portions of the generic input data may be returned for each occurrence of the term within the predetermined classification scheme. Once the mapping has been completed, the input generic data can be scored, step 525. Scoring may include, for example, using string-dissimilarity techniques that utilize stemmed and literal forms of input text to compare the input string from a given free-text input field to a relatively small set of target candidates.

In other embodiments, such as, for example, when scoring medications, the techniques in place in the NLPR may be used to normalize the parts of the medication expressions, such as, for example. frequency, dosage, and route of administration. Any other compact scoring system may be used in connection with the present invention. Scoring may be further simplified by permitting users to identify scoring errors and emissions and provide feedback to the system to permit the system to effectively adapt to correct an error or omission. In an embodiment of the invention, once the data has been scored, the n-best results may be retrieved, step 530. In an alternative embodiment, the number of results that may be returned include all classifications that exceed a predetermined threshold score.

After the n-best codes are retrieved, step 530, the user may be presented with feedback, step 540, such as, for example, a pop-up window including the relevant classifications of information. Feedback may be any type of user-perceptible feedback. The relevant classifications may be presented in the form of, for example, billing codes. The billing codes may be associated with, for example, CPT-4 billing codes. In an alternative embodiment, prior to presenting the user with feedback, the returned billing codes may be filtered, step 536, through a subset of the predetermined classification scheme associated with, for example, the billing physician, step 535. In this embodiment, the predetermined classification scheme can include a number of medical billing codes and the subset of the predetermined classification scheme can include medical billing codes associated with a particular physician or group of physicians. The predetermined classification scheme may utilize latent information to determine the applicability of particular billing codes to a given encounter. If the n-best results retrieved in step 530 include billing codes that are not appropriate for a particular physician, for example, these codes may be filtered out using filter 536 in step 535 prior to providing feedback to the user, step 540.

After the feedback has been provided to the user, the user may input data based on the feedback. The information input by the user may be stored in, for example, an NLPR database 545. In one embodiment, using, for example, an out-patient superbill environment (i.e., an environment in which a physician or member of the physician's staff fills out a single form that encapsulates relevant patient information and both the billing codes and encounter data supporting these billing codes), NLPR data may be sent directly to output 555, and a bill may be produced directly. In an alternative embodiment, data from the NLPR may be sent to be further manipulated, step 550, prior to generating, for example, a patient bill, step 555. In addition to being input into, for example, a billing environment, data from the NLPR may be input into, for example a clinical data repository (CDR) and/or an electronic medical record (EMR), step 560. Various other types of outputs and storage for data are known and may be applied at step 560.

An example of the application of the methods and systems according to the embodiment illustrated in FIG. 5 will be described with reference to a medical billing system. Generic data regarding a patient encounter may be input, step 510. This information may include medical problems treated by an attending physician, and may also include medical procedures or treatments that were performed. These medical problems may then be normalized to, for example, the SNOMED CT nomenclature, step 515. These normalized terms can then be mapped against a predetermined classification scheme, step 520, such as, for example, the ICD-9 classification, as described above. The ICD-9 classification may return a number of codes associated with particular treatments or medical problems. In an alternative embodiment, the normalized terms may be mapped against the CPT-4 classification. In yet another embodiment, the data may be used to compute a Medicare E&M level code. Once the codes have been returned based on the mapping of the normalized generic data, the codes may be ranked based on a scoring of the normalized data against the predetermined classification scheme. Based on the scoring, the user may be presented with feedback, such as, for example, a pop-up window that presents the n-best ranked codes. In one embodiment, these codes have been filtered against a subset, of billing codes associated with the billing physician, step 535. Once the feedback has been provided to the user, step 540, the user may input data based on the feedback into the NLPR database 545 for a particular patient record. In one embodiment, the billing codes may be sent directly to a billing system, (e.g., output 555) for the generation of patient, bills. This embodiment may be utilized in an out-patient superbill environment. In an alternative embodiment, the data input into the NLPR may be further processed and coded, step 550, by, for example, a buffing coder. Then the billing codes generated through the additional manipulation of the data may be sent to the billing system. Additionally, the information from the NLPR may be sent to a clinical data repository (CDR) and/or an electronic medical record (EMR), step 560. While various embodiments of the invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

For example, while the invention was described with reference to a medical environment, such as a hospital or an out-patient environment, the invention is equally applicable in an environment requiring the maintenance of accurate records. The present invention may be configured to be used in connection with any constrained data input tasks in a variety of non-medical environments.

Furthermore, while particular embodiments of the invention were described with respect to the use of predetermined templates associated with, for example, billing codes for CPT-4, ICD-9, JCAHO-based reporting requirements, and E&M billing, any number of other templates may be constructed and utilized in accordance with the present invention. In one embodiment, an institution may create custom predefined templates that their employees may use to maintain accurate and complete records for virtually any constrained data input task.

What is claimed is:

1. At least one computer-readable storage medium having instructions encoded thereon which, when executed, perform a method comprising acts of:
   receiving an input data stream comprising speech data documenting a physician's encounter with a patient, the input data stream comprising latent information associated with a type of medical report appropriate for documenting the encounter with the patient;
   processing the input data stream to identify the latent information;
   based on the identified latent information, identifying the type of medical report appropriate for documenting the encounter with the patient;
   activating a template specific to the identified type of medical report appropriate for documenting the encounter with the patient, wherein the template specifies at least a plurality of data fields required for documenting the encounter with the patient;
   obtaining, from the input data stream, information corresponding to at least one of the data fields specified by the activated template; and
   populating the template with the obtained information to generate a medical report that documents the encounter with the patient.

2. The at least one computer-readable storage medium of claim 1, wherein the report comprises an accreditation report or a billing report.

3. The at least one computer-readable storage medium of claim 1, wherein the latent information comprises information about at least one medical fact selected from the group consisting of a medical problem, an allergy, a medical treatment, a medication and a medical procedure.

4. The at least one computer-readable storage medium of claim 1, wherein the act of activating the template comprises selecting a template from a group of stored templates and activating the selected template.

5. The at least one computer-readable storage medium of claim 1, wherein the act of obtaining the information corresponding to at least one of the data fields specified by the activated template comprises prompting a user for the information.

6. The at least one computer-readable storage medium of claim 5, wherein the user is the physician.

7. The at least one computer-readable storage medium of claim 1, wherein the template is activated based on the latent information that does not specify the type of report to which the template relates.

8. A system comprising at least one processor programmed to:
   receive an input data stream comprising speech data documenting a physician's encounter with a patient, the input data stream comprising latent information associated with a type of medical report appropriate for documenting the encounter with the patient;
   process the input data stream to identify the latent information;
   based on the identified latent information, identify the type of medical report appropriate for documenting the encounter with the patient;
   activate a template specific to the identified type of medical report appropriate for documenting the encounter with the patient, wherein the template specifies at least a plurality of data fields required for documenting the encounter with the patient;
   obtain, from the input data stream, information corresponding to at least one of the data fields specified by the activated template; and
   populate the template with the obtained information to generate a medical report that documents the encounter with the patient.

9. The system of claim 8, wherein the report comprises an accreditation report or a billing report.

10. The system of claim 8, wherein the latent information comprises information about at least one medical fact selected from the group consisting of a medical problem, an allergy, a medical treatment, a medication and a medical procedure.

11. The system of claim 8, further comprising at least one memory that stores a group of templates including the template, and wherein the at least one processor is programmed to activate the template by selecting the template from the stored group of templates and activating the selected template.

12. The system of claim 8, wherein the at least one processor is programmed to obtain the information corresponding to at least one of the data fields specified by the activated template at least in part by prompting a user to provide the information.

13. The system of claim 12, wherein the user is the physician.

14. The system of claim 8, wherein the at least one processor is programmed to activate the template based on the latent information that does not specify the type of report to which the template relates.

* * * * *